(12) United States Patent
Dierker et al.

(10) Patent No.: US 8,518,385 B2
(45) Date of Patent: Aug. 27, 2013

(54) ANTIPERSPIRANT COMPOSITION BASED ON DICARBOXYLIC ACID DIESTERS OF A C6-C18 DICARBOXYLIC ACID WITH C12-C22 FATTY ALCOHOLS

(75) Inventors: Markus Dierker, Duesseldorf (DE); Catherine Weichold, Aachen (DE); Michael Neuss, Cologne (DE); Ulrich Issberner, Ambler, PA (US)

(73) Assignee: Cognis IP Management GmbH, Duesseldorf (DE)

( * ) Notice: Subject to any disclaimer, the term of this patent is extended or adjusted under 35 U.S.C. 154(b) by 953 days.

(21) Appl. No.: 11/886,621

(22) PCT Filed: Mar. 20, 2006

(86) PCT No.: PCT/EP2006/002529
§ 371 (c)(1),
(2), (4) Date: Dec. 22, 2008

(87) PCT Pub. No.: WO2006/097334
PCT Pub. Date: Sep. 21, 2006

(65) Prior Publication Data
US 2009/0214457 A1  Aug. 27, 2009

(30) Foreign Application Priority Data
Mar. 18, 2005 (DE) .......................... 10 2005 013 068

(51) Int. Cl.
*A61K 8/28* (2006.01)
*A61K 8/58* (2006.01)
*A61Q 15/00* (2006.01)

(52) U.S. Cl.
USPC .......................................................... 424/66

(58) Field of Classification Search
USPC .......................................................... 424/66
See application file for complete search history.

(56) References Cited

U.S. PATENT DOCUMENTS

| | | | |
|---|---|---|---|
| 4,126,679 A | 11/1978 | Davy et al. | |
| 4,151,001 A * | 4/1979 | Anderson et al. | 106/270 |
| 4,822,603 A | 4/1989 | Farris et al. | |
| 2002/0018760 A1 * | 2/2002 | Vatter et al. | 424/70.12 |
| 2004/0022822 A1 * | 2/2004 | Poret | 424/401 |
| 2004/0223995 A1 | 11/2004 | Emslie et al. | |
| 2005/0255064 A1 | 11/2005 | Bruening et al. | |
| 2006/0147390 A1 * | 7/2006 | Schreiber et al. | 424/47 |

FOREIGN PATENT DOCUMENTS

| | | |
|---|---|---|
| DE | 101 62 049 A1 | 6/2003 |
| EP | 0 117 070 B1 | 8/1990 |
| EP | 0 585 981 A1 | 3/1994 |
| EP | 0585981 A1 * | 9/1994 |
| EP | 0 970 998 A1 | 1/2000 |
| EP | 1 161 937 A2 | 12/2001 |
| EP | 1 334 712 A2 | 8/2003 |
| EP | 0585981 A1 * | 9/2003 |
| FR | 2 857 589 A1 | 1/2005 |

OTHER PUBLICATIONS

Melting Points, ChemicalLand21, http://www.chemicalland21.com/industrialchem/IUH/OCTADECANEDIOIC%20ACID.htm.*
McGee et al., J Chem Engineering Data 7: 102 (1962).*
Davies, Trans Faraday Soc p. 909 (1948).*

* cited by examiner

*Primary Examiner* — James H Alstrum Acevedo
*Assistant Examiner* — Thor Nielsen
(74) *Attorney, Agent, or Firm* — Servilla Whitney LLC

(57) ABSTRACT

A composition for cosmetic compositions which contains (a) at least one dicarboxylic acid diester of a C6-C13 dicarboxylic acid with a C12-22 fatty alcohol; (b) at least one oil component. The composition provides excellent antiperspirant and deodorant sticks when combined with an antiperspirant or deodorizing composition. Addition of a pigment provides cosmetic sticks such as lipsticks. The composition can be water free.

15 Claims, No Drawings

ANTIPERSPIRANT COMPOSITION BASED ON DICARBOXYLIC ACID DIESTERS OF A C6-C18 DICARBOXYLIC ACID WITH C12-C22 FATTY ALCOHOLS

CROSS-REFERENCE TO RELATED APPLICATIONS

This application is filed under 35 U.S.C. §371 claiming priority from Application PCT/EP2006/002529 filed on Mar. 20, 2006, which claims priority of German Application No. 10 2005 013 068.2 filed Mar. 18, 2005, the entire contents of which are incorporated herein by reference.

FIELD OF THE INVENTION

This invention relates to water-free compositions which contain at least one dicarboxylic acid diester of a C6-C18 dicarboxylic acid with C12-C22 fatty alcohols and which have a melting point of at least 30° C.

BACKGROUND OF THE INVENTION

Cosmetic stick compositions are known among experts in many forms, for example as antiperspirant sticks, lipsticks or make-up sticks. Relatively long-chain fatty alcohols (such as Lanette® 18 for example) or ricinoleic acid derivatives (Edenor® OSSG, Cutina® HR) are normally used as consistency factors for stick compositions. Stick compositions based on fatty compounds with a defined melting point are known, for example, from EP 1 161 937 A. The use of long-chain wax-like C16-C60 dialkyl carbonates in water-free antiperspirant compositions is known from DE 101 62 049.

In recent years, water-free cream and stick preparations have found increasing acceptance on the cosmetics market. Fatty alcohols, such as for example cetearyl, stearyl and behenyl alcohol, and hydroxyfatty acids, for example 12-hydroxystearic acid, have frequently been used as a so-called wax base for water-free antiperspirant sticks and so-called soft solid formulations. Corresponding stick preparations are disclosed, for example in U.S. Pat. No. 4,822,603, in U.S. Pat. No. 4,126,679 and in EP 117 070.

Water-free stick preparations containing volatile silicone oils have the disadvantage that the dispersed active components lead to visible product residues on the skin and clothing. If pressure is applied during application, "oiling out" (syneresis) often occurs and reduces the cosmetic acceptance of the preparations among users. In addition, the fatty alcohol base leaves the skin with an unsatisfactory feeling and frequently causes dermal irritation, even if the other emollients are optimally selected.

The problem addressed by the present invention was to provide consistency factors with better sensory properties for water-free stick compositions which would provide the stick compositions with the necessary hardness and which would give smooth stick surfaces with an attractive gloss that would be less inclined to "crumble" than known products.

It has surprisingly been found that this problem can be purposefully solved by certain dicarboxylic acid diesters.

BRIEF DESCRIPTION OF THE INVENTION

Accordingly, the present invention relates to water-free cosmetic compositions with a melting point of at least 30° C. containing
(a) at least one dicarboxylic acid diester of a C6-C18 dicarboxylic acid with C12-C22 fatty alcohols,
(b) at least one oil component,
(c) at least one inorganic astringent salt, a deodorant component or a pigment.

DETAILED DESCRIPTION OF THE INVENTION

Water-free compositions in the context of the present invention are compositions which contain less than 5% by weight water (not including water of crystallization), preferably less than 2% by weight water and, more particularly, less than 1% by weight water. A residual water content may emanate from the raw materials used and may therefore be unavoidable.

The specific dicarboxylic acid diesters are very good consistency factors in water-free cosmetic formulations. According to the invention, a single dicarboxylic acid diester or a mixture of dicarboxylic acid diesters or a mixture of the dicarboxylic acid diesters with commercially available consistency factors, such as fatty alcohols etc., may be used. These esters are particularly suitable for use in antiperspirant/deodorant sticks. They provide the stick compositions with the necessary hardness and with a smooth stick surface having an attractive gloss which is less inclined to "crumble". In one particularly preferred embodiment, the stick compositions are free from silicone oils, more particularly readily volatile silicone oils, such as cyclomethicone.

Achieving the requisite hardness requires a smaller percentage content of the specific dicarboxylic acid diester in the stick formulation by comparison with fatty alcohols, such as Lanette® 18. The specific dicarboxylic acid diesters are compatible with numerous emollients, such as for example Cetiol® OE, Cetiol® CC, and with cyclomethicone or hydrocarbons, such as Arlamol® HD, Synfluid® PAO. Silicone-free stick compositions and deodorants can also be produced. The specific dicarboxylic acid diesters are not hydrolyzed by the strong Lewis acids which are generally used in antiperspirant formulations (for example aluminum chloride, aluminum chlorohydrate, zirconium salts and mixtures thereof. This also applies to their use in water-containing antiperspirant formulations. By comparison with the usual thickeners, such as Lanette® 18 or Cutina® HR (hydrogenated castor oil), the dicarboxylic acid diesters contain no free OH groups which could lead to reactions with the Lewis acids.

The dicarboxylic acid component of the dicarboxylic acid diester is selected from C6-C18 dicarboxylic acids, of which the most important representatives include adipic acid, azelaic acid, sebacic acid, dodecanedioic acid and octadecanedioic acid. In a preferred embodiment of the invention, the dicarboxylic acid component is selected from unbranched, saturated C6-C18 dicarboxylic acids, preferably from unbranched, saturated C9-C18 dicarboxylic acids and, more particularly, from unbranched, saturated C12-C18 dicarboxylic acids.

The alcohol component of the esters may be selected from the usual C12-C22 fatty alcohols, for example dodecanol, tridecanol, tetradecanol, pentadecanol, hexadecanol, heptadecanol, octadecanol, octadecenol, nonadecanol, eicosanol, eicosenol, heneicosanol, docosanol and docosenol. Technical mixtures of primary alcohols as obtained from natural fats and oils by standard oleochemical methods may also be used in accordance with the invention. Unbranched, saturated C16-C22 fatty alcohols, more particularly C16-C18 fatty alcohols, are preferably used in accordance with the invention.

In a preferred embodiment, the composition contains a dicarboxylic acid diester with a melting point of at least 50° C. and preferably in the range from 50 to 55° C.

The composition according to the invention contains at least one inorganic astringent salt, a deodorant component or a pigment as component (c), depending on whether the composition is a stick composition for antiperspirants/deodorants or decorative cosmetics.

Pigments

Suitable pigments are any of the oxides and pigments typically used in lipsticks, eye shadow sticks and make-up sticks, such as for example titanium dioxide, iron oxides, zinc oxide, mica pigments or pearlescent pigments of which the optical effect is based on a combination of transparency and interference. The latter pigments are made up on the layer/substrate principle of the optically neutral carrier substance, mica, and an optically active metal oxide layer (layer/substrate pigments). The development of the pearlescent effect or interference effect is critically dependent on a sufficiently large difference between the refractive index of the mica (n=1.5) and that of the metal oxide (n=2.5-2.7). The pearlescent pigments are divided into titanium dioxide/mica pigments, titanium dioxide/iron oxide/mica pigments and iron oxide/mica pigments.

Metal oxide/mica pigments are dry powders with a density of ca. 3 g/cm$^3$. They are generally heat-resistant up to 800° C. The pearlescent effect is determined by the nature of the metal oxide and its layer thickness on the mica. The pigments are more or less transparent. Their gloss and covering power are dependent on the particle size distribution, for example <15 μm, 5-25 μm, 10-60 μm or 20-100 μm.

Titanium dioxide/mica pigments are the most important group of pearlescent pigments. On the mica platelets, there is a 40 to 60 nm thick layer of titanium dioxide of the anatase modification or rutile modification. The pigments are white and lead to fine, silky effects (fine particles) or coarse glitter effect (coarse particles). Pigments with a relatively high titanium dioxide layer thickness (60 to 160 nm) act as interference pigments.

In titanium dioxide/iron oxide/mica pigments, there is a layer of iron oxide on the layer of titanium dioxide. Depending on the layer thickness of the metal oxides, this results is light golden, reddish golden or greenish golden bright color pigments of which the covering power is distinctly increased by the iron oxide.

If the mica is directly coated with iron oxide, brown to red-brown iron oxide/mica pigments with further improved covering power are obtained. The color tones vary between bronze, copper, red to red-green, depending on the layer thickness of the iron oxide.

Titanium dioxide/iron titanate/mica pigments are sliver-gray, blue-gray and anthacite-colored. Inclusions of carbon black in the titanium dioxide layer also lead to gray pigments. Other color tones can be obtained by coating the titanium dioxide layer with iron blue or organic substances, such as carmine red.

The present invention also relates to the use of dicarboxylic acid diesters of a C6-C18 dicarboxylic acid with C12-C22 fatty alcohols in stick compositions for decorative cosmetics. These include make-up sticks, eye shadow sticks and, in particular, lipsticks.

Inorganic Astringent Salt: Antiperspirant Component

In principle, any inorganic astringent salts which reduce perspiration are suitable as the antiperspirant component. According to the invention, these salts are preferably astringent aluminum compounds, aluminum zirconium compounds, aluminum or zinc salts. Examples include aluminum chloride, aluminum chlorohydrate, aluminum dichlorohydrate, aluminum sesquichlorohydrate and complex compounds thereof, for example with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, for example with amino acids, such as glycine. Aluminum chlorohydrate, aluminum zirconium tetrachlorohydrate, aluminum zirconium pentachlorohydrate and complex compounds thereof are preferably used. The use of compounds commercially available as Locron® P and Rezal® 36 GP is particularly preferred.

A preferred embodiment of the invention is a composition containing (a) 5 to 40% by weight of at least one diester of a C6-C18 dicarboxylic acid with C12-C22 fatty alcohols, (b) 30 to 80% by weight of at least one oil component and (c) 10 to 40% by weight of at least one antiperspirant component. A particularly preferred composition is one containing (a) 8 to 25% by weight of at least one diester of a C6-C18 dicarboxylic acid with C12-C22 fatty alcohols, (b) 40 to 70% by weight of at least one oil component and (c) 15 to 30% by weight of at least one antiperspirant component and, more particularly, (a) 12 to 20% by weight of at least one diester of a C6-C18 dicarboxylic acid with C12-C22 fatty alcohols, (b) 50 to 60% by weight of at least one oil component and (c) 15 to 25% by weight of at least one antiperspirant component.

The present invention also relates to the use of dicarboxylic acid diesters of a C6-C18 dicarboxylic acid with C12-C22 fatty alcohols in antiperspirant compositions. These compositions may be both water-containing and "water-free" as defined in the foregoing. More particularly, the present invention relates to the use of dicarboxylic acid diesters of a C6-C18 dicarboxylic acid with C12-C22 fatty alcohols for the production of water-free antiperspirant compositions. The present invention also relates to the use of dicarboxylic acid diesters of a C6-C18 dicarboxylic acid with C12-C22 fatty alcohols for improving the consistency of antiperspirant and deodorant sticks.

After a penetration time of 5 seconds at 23° C., the preparations according to the invention preferably have a penetration depth of less than 5 mm and preferably in the range from 2.4 to 4 mm (Penetrometer PNR 10 Petrotest; Petrotest Instruments GmbH & Bo. KG; microcone: 5.0 g; drop bar: 47.5 g; measuring temperature: 23° C.; measuring time: 5 seconds). The penetration depth is thus a measure of the "hardness" or consistency of the preparation. The lower the depth of penetration, the "harder" the antiperspirant.

Deodorant Components

A number of very different classes of compound may be used as the deodorant components. They are preferably used in combination with antiperspirant components to achieve optimal all-round performance, i.e. a long-lasting cascade effect.

Esterase Inhibitors

Where perspiration is present in the axillary region, extracellular enzymes—esterases, preferably proteases and/or lipases—are formed by bacteria, cleave the esters present in the perspiration and thus release odor-forming substances. Substances which inhibit enzyme activity and thereby reduce odor formation include trialkyl citrates, such as trimethyl citrate, tripropyl citrate, triisopropyl citrate, tributyl citrate and, in particular, triethyl citrate (Hydagen® C.A.T., Cognis GmbH, Düsseldorf/FRG). The free acid is probably released through the cleavage of the citric acid ester, reducing the pH value of the skin to such an extent that the enzymes are inactivated by acylation. Other substances suitable as esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester and zinc glycinate.

The compositions according to the invention may contain the esterase inhibitors in quantities of 0.01 to 20% by weight, preferably in quantities of 0.1 to 10% by weight and more particularly in quantities of 0.5 to 5% by weight, based on the composition as a whole.

Bactericidal or Bacteriostatic Components

Typical examples of suitable bactericidal or bacteriostatic components are chitosan and phenoxyethanol. 5-Chloro-2-(2,4-dichloro-phenoxy)-phenol, which is marketed under the name of Irgasan® by Ciba-Geigy of Basel, Switzerland, has also proved to be particularly effective.

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers. Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

The compositions according to the invention may contain the bactericidal/bacteriostatic or germ-inhibiting components in quantities of 0.01 to 10% by weight, preferably in quantities of 0.1 to 5% by weight and more particularly in quantities of 0.5 to 2% by weight.

Besides these deodorant components, odor absorbers are often also used. Odor absorbers are substances which are capable of absorbing and largely retaining the odor-forming compounds, but are not active against bacteria. They reduce the partial pressure of the individual components and thus also reduce the rate at which they spread. Odor absorbers should not affect the perfume note of a perfume. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, chamomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Besides the deodorant components, perspiration-absorbing substances are often also used and include modified starch, for example, Dry Flo® Plus (National Starch), silicates, talcum, bentonite, montmorillonite, hectorite and other substances of similar modification which appear suitable for absorbing perspiration.

Oil Components

The composition according to the invention contains at least one oil component. In the context of the invention, oil components are substances or mixtures of substances which are liquid at 20° C. and immiscible with water at 25° C. Such substances include, for example, glycerides, hydrocarbons, silicone oils, ester oils, dialkyl(ene) ethers, dialkyl(ene) carbonates liquid at 20° C. or mixtures thereof. The oil components are present in the compositions according to the invention in total quantities of normally 30 to 80% by weight, preferably 40 to 70% by weight and more particularly 50 to 60% by weight, based on the composition as a whole.

Glycerides suitable as oil components in accordance with the invention include fatty acid esters of glycerol liquid at 20° C. which may be of natural (animal and vegetable) or synthetic origin. Glycerides are divided into mono-, di- and triglycerides. They are known substances which may be obtained by the relevant methods of preparative organic chemistry. Synthetic glycerides are normally mixtures of mono-, di and triglycerides which are obtained by transesterification of the corresponding triglycerides with glycerol or by selective esterification of fatty acids. Preferred fatty acids for the purposes of the invention are $C_{6-24}$ fatty acids and, among these, $C_{6-18}$ fatty acids and especially $C_{8-18}$ fatty acids. The fatty acids may be branched or unbranched, saturated or unsaturated. According to the invention, it is preferred to use glycerides of vegetable origin liquid at 20° C., more particularly cocoglycerides, a mixture of predominantly di- and triglycerides with $C_{8-18}$ fatty acids marketed under the name of Myritol® 331 by Cognis Deutschland GmbH. It is also preferred to use Myritol® 312 ($C_{8/10}$ triglycerides), Cegesoft® PS 17, Cegesoft® GPO, Cegesoft® PFO and Cegesoft® PS 6.

A preferred embodiment of the invention contains at least one oil component selected from the group of dialkyl ethers, dialkyl carbonates, hydrocarbons or a mixture of these substances. Oil components such as these provide the compositions with particularly good skin-care and sensory properties and a pleasantly dry feeling on the skin after application. The combination of a dialkyl ether with cyclohexane derivatives is also preferred. A particularly preferred oil component combination for the compositions according to the invention contains Cetiol® OE and Cetiol® S.

Other suitable oil components are Guerbet alcohols liquid at 20° C. based on fatty alcohols containing 6 to 18 and preferably 8 to 10 carbon atoms, such as Eutanol® G for example. Liquid esters of linear, saturated or unsaturated $C_{6-22}$ fatty acids with linear or branched, saturated or unsaturated $C_{6-22}$ fatty alcohols or esters of branched $C_{6-13}$ carboxylic acids with linear or branched, saturated or unsaturated $C_{6-22}$ fatty alcohols, such as Cetiol® CC for example, may also be used as oil components in accordance with the invention.

Examples of wax esters liquid at 20° C. include the following typical representatives: decyl oleate (Cetiol® V), cococaprylate/caprate (Cetiol® SN), hexyl laurate (Cetiol® A), myristyl isostearate, myristyl oleate, cetyl isostearate, cetyl oleate, stearyl isostearate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate (Cetiol® DAB), oleyl behenate, oleyl erucate (Cetiol® J 600), behenyl isostearate, erucyl isostearate, erucyl oleate. Also suitable are esters of linear $C_{6-22}$ fatty acids with branched alcohols, more particularly 2-ethyl hexanol (Cetiol® 868), esters of $C_{18-38}$ alkylhydroxycarboxylic acids with linear or branched $C_{6-22}$ fatty alcohols, esters of linear and/or branched fatty acids with polyhydric alcohols (for example propylene glycol, dimer diol or trimer triol) and esters of $C_{6-22}$ fatty alcohols and/or Guerbet alcohols with aromatic carboxylic acids, more particularly benzoic acid Other oil components suitable for use in accordance with the invention are natural and synthetic, aliphatic and/or naphthenic hydrocarbons liquid at 20° C., such as for example squalane, squalene, paraffin oils, isohexadecane, isoeicosane or polydecenes and dialkyl cyclohexanes (Cetiol® S).

Waxes

In another preferred embodiment, the compositions according to the invention contain at least one other wax which contributes towards optimizing the sensory properties, the consistency and the stability of the sticks. According to the invention, this other wax (for a definition, see Römpp Chemie Lexikon) may be selected from any natural and synthetic substances of wax-like consistency. These include inter alia fats (triglycerides), mono- and diglycerides, waxes, fatty and wax alcohols, fatty acids, esters of fatty alcohols and also fatty acid amides or mixtures of these substances. They may be present in the compositions according to the invention in a total quantity of 0.1 to 40% by weight, preferably 1 to 30% by weight and more particularly 5 to 20% by weight, based on the composition as a whole. Relatively long-chain fatty alcohols (such as, for example, Lanette® 18 and Lanette® 22) or ricinoleic acid derivatives (Edenor® OSSG, Cutina® HR) are preferably used as additional waxes for the stick compositions according to the invention.

EXAMPLES

TABLE 1

Melting points of the dicarboxylic acid diesters

| | | Alcohol component used | | |
|---|---|---|---|---|
| Dicarboxylic acid | | Lorol Spezial | Stenol 16-18 | Stenol C1822AT |
| Adipic acid | C 6 | 33° C. | 51-55° C. | 53-60° C. |
| Azelaic acid | C 9 | 35-36.5° C. | 54-55° C. | 57-66° C. |
| Sebacic acid | C 10 | 37-39° C. | 53-58° C. | 65-68° C. |
| Dodecanedioic acid | C 12 | 42-44° C. | 59-61° C. | 64-68° C. |
| Octadecanoic acid | C 18 | — | 66-69° C. | 73-76° C. |

TABLE 2

Acid values of the dicarboxylic acid diesters

| | | Alcohol component used | | |
|---|---|---|---|---|
| Dicarboxylic acid | | Lorol Spezial | Stenol 16-18 | Stenol C1822AT |
| Adipic acid | C 6 | 0.8 | 1.0 | 0.8 |
| Azelaic acid | C 9 | 0.8 | 0.8 | 1.2 |
| Sebacic acid | C 10 | 1.0 | 0.5 | 0.8 |
| Dodecanedioic acid | C 12 | 0.9 | 1.0 | 0.3 |
| Octadecanoic acid | C 18 | — | 0.5 | 0.4 |

TABLE 3

OH values of the dicarboxylic acid diesters

| | | Alcohol component used | | |
|---|---|---|---|---|
| Dicarboxylic acid | | Lorol Spezial | Stenol 16-18 | Stenol C1822AT |
| Adipic acid | C 6 | 3.2 | 5.0 | 2.0 |
| Azelaic acid | C 9 | 1.4 | 1.1 | 0.6 |
| Sebacic acid | C 10 | 1.2 | 3.6 | 2.1 |
| Dodecanedioic acid | C 12 | 1.2 | 0.3 | 0.9 |
| Octadecanoic acid | C 18 | — | 5.0 | 2.0 |

TABLE 4

General composition of an antiperspirant stick

| | 1 | 2 |
|---|---|---|
| Dicarboxylic acid diester | 12.00 | 20.00 |
| DC ® 245 | 37.00 | 33.00 |
| Cetiol ® OE | 10.00 | 9.00 |
| Cetiol ® S | 18.00 | 15.00 |
| Rezal ® 36GP | 23.00 | 23.00 |

TABLE 5

Stick hardnesses, cf. composition 1 in Table 4

| | Alcohol component used | | |
|---|---|---|---|
| | Lorol Spezial $C_{12-14}$ | Stenol 16-18 $C_{16-18}$ | Stenol C1822 AT $C_{18-22}$ |
| Adipic acid $C_6$ | — | 4.70 | 4.47 |
| Azelaic acid $C_9$ | — | — | 4.50 |

TABLE 5-continued

Stick hardnesses, cf. composition 1 in Table 4

| | | Alcohol component used | | |
|---|---|---|---|---|
| | | Lorol Spezial $C_{12-14}$ | Stenol 16-18 $C_{16-18}$ | Stenol C1822 AT $C_{18-22}$ |
| Sebacic acid | $C_{10}$ | — | 5.51 | 4.10 |
| Dodecanedioic acid | $C_{12}$ | 7.45 | 4.87 | 3.38 |
| Octadecanedioic acid | $C_{18}$ | — | — | 3.69 |

TABLE 6

Stick hardnesses, cf. composition 2 in Table 4

| | | Alcohol component used | | |
|---|---|---|---|---|
| | | Loral Spezial $C_{12-14}$ | Stenol 16-18 $C_{16-18}$ | Stenol C1822 AT $C_{18-22}$ |
| Adipic acid | $C_6$ | — | 2.60 | 2.36 |
| Azelaic acid | $C_9$ | — | — | 2.38 |
| Sebacic acid | $C_{10}$ | 8.86 | 4.70 | 1.99 |
| Dodecanedioic acid | $C_{12}$ | 2.80 | 2.71 | 2.63 |
| Octadecanedioic acid | $C_{18}$ | — | — | 1.80 |

TABLE 7

Antiperspirant/deodorant sticks

| | 3 | 4 | 5 |
|---|---|---|---|
| Adipic acid di-12/14-ester | 4.00 | 4.00 | |
| Adipic acid di-Lanette 0 | 16.00 | | |
| Adipic acid di-18/22-ester | | 16.00 | |
| Azelaic acid di-12/14-ester | | | 4.00 |
| Sebacic acid 18/22-ester | | | 16.00 |
| Dow Corning ® 245 | 33.00 | 33.00 | 33.00 |
| Cetiol ® OE | 9.00 | 9.00 | 9.00 |
| Cetiol ® S | 15.00 | 15.00 | 15.00 |
| Rezal ® 36GP | 23.00 | 23.00 | 23.00 |
| Hardness | | | |
| $1^{st}$ day | 4.55 | 3.59 | 3.77 |

TABLE 8

| | 1 | 2 | 3 |
|---|---|---|---|
| Ingredients | | | |
| Dodecandioic acid 16/18-diester | 8.00 | 8.00 | 16.00 |
| Cutina ® HR | 4.00 | | |
| Edenor ® OSSG | | 4.00 | |
| Lanette ® 18 | | | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness | | | |
| Initial Structure, initial | 8.38 | 4.43 | 3.07 |
| Surface | flat, mushy | sparkling, white | sparkling |
| Rub-off | crumbly, very white | slightly crumbly | slightly white |
| Cut surface | flat, coarse | fine, white | fine, flat |

TABLE 9

| | 4 | 5 | 6 |
|---|---|---|---|
| Ingredients | | | |
| Adipic acid di-Lanette O 16/18 | 8.00 | 8.00 | 16.00 |
| Cutina ® HR | 4.00 | | |
| Edenor ® OSSG | | 4.00 | |
| Lanette ® 18 | | | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness | | | |
| Initial Structure, initial | 5.34 | 5.86 | 5.6 |
| Surface | flat, very white | sparkling | hangs from lid |
| Rub-off | very white, high rub-off, crumbly | slightly white | slightly white |
| Cut surface | crumbly, coarse | crumbly, fine | flat, fine |

TABLE 10

| | 7 | 8 | 9 |
|---|---|---|---|
| Ingredients | | | |
| Azelaic acid di-16/18-ester | 8.00 | 8.00 | 16.00 |
| Cutina ® HR | 4.00 | | |
| Edenor ® OSSG | | 4.00 | |
| Lanette ® 18 | | | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness | | | |
| Initial Structure, initial | 4.19 | 4.56 | 2.91 |
| Surface | flat | flat | slightly sparkling |
| Rub-off | white, crumbly | white, crumbly | white, slightly crumbly |
| Cut surface | fine, crumbly | fine, flat | fine, flat |

TABLE 11

| | 10 | 11 | 12 |
|---|---|---|---|
| Ingredients | | | |
| Adipic acid di-18/22-ester | 8.00 | 8.00 | 16.00 |
| Cutina ® HR | 4.00 | | |
| Edenor ® OSSG | | 4.00 | |
| Lanette ® 18 | | | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness | | | |
| Initial Structure, initial | 38.01 | 4.38 | 2.87 |
| Surface | mushy | sparkling | sparkling |
| Rub-off | very white | slightly white, creamy | white, creamy |
| Cut surface | crumbly, coarse, mushy | fine, flat | fine, flat |

TABLE 12

|  | 13 | 14 | 15 |
|---|---|---|---|
| Ingredients |  |  |  |
| Azelaic acid di-18/22-ester | 8.00 | 8.00 | 16.00 |
| Cutina ® HR | 4.00 |  |  |
| Edenor ® OSSG |  | 4.00 |  |
| Lanette ® 18 |  |  | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness |  |  |  |
| Initial | 6.38 | 4.33 | 4.14 |
| Structure, initial |  |  |  |
| Surface | slightly crumbly | partly sparkling | sparkling |
| Rub-off | very white, mushy | slightly white | white, slightly crumbly |
| Cut surface | fine, crumbly | fine, flat | fine, flat |

TABLE 13

|  | 16 | 17 | 18 |
|---|---|---|---|
| Ingredients |  |  |  |
| Sebacic acid di-18/22-ester | 8.00 | 8.00 | 16.00 |
| Cutina ® HR | 4.00 |  |  |
| Edenor ® OSSG |  | 4.00 |  |
| Lanette ® 18 |  |  | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness |  |  |  |
| Initial | 3.99 | 4.27 | 3.54 |
| Structure, initial |  |  |  |
| Surface | flat | partly sparkling white, slightly crumbly | partly sparkling white, slightly crumbly |
| Rub-off | very white, mushy |  |  |
| Cut surface | crumbly, coarse | fine, flat | fine, flat |

TABLE 14

|  | 19 | 20 | 21 |
|---|---|---|---|
| Ingredients |  |  |  |
| C12-Dicarboxylic acid di-18/22-ester | 8.00 | 8.00 | 16.00 |
| Cutina ® HR | 4.00 |  |  |
| Edenor ® OSSG |  | 4.00 |  |
| Lanette ® 18 |  |  | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness |  |  |  |
| Initial | 4.51 | 4.61 | 3.34 |
| Structure, initial |  |  |  |
| Surface | flat | flat, partly sparkling | sparkling |
| Rub-off | white, slightly crumbly | white, slightly crumbly | white, slightly crumbly |
| Cut surface | fine, flat | fine, flat | fine, flat |

TABLE 15

|  | 22 | 23 | 24 |
|---|---|---|---|
| Ingredients |  |  |  |
| DCA: O di-Stenol 18/22-ester | 8.00 | 8.00 | 16.00 |
| Cutina ® HR | 4.00 |  |  |
| Edenor ® OSSG |  | 4.00 |  |
| Lanette ® 18 |  |  | 4.00 |
| DC ® 245 | 37.00 | 37.00 | 33.00 |
| Cetiol ® OE | 10.00 | 10.00 | 9.00 |
| Cetiol ® S | 18.00 | 18.00 | 15.00 |
| Rezal ® 36GP | 23.00 | 23.00 | 23.00 |
| Hardness |  |  |  |
| Initial | 4.01 | 4.41 | 2.99 |
| Structure, initial |  |  |  |
| Surface | flat, very white | flat | sparkling, flat |
| Rub-off | crumbly | creamy white, fine | white, slightly crumbly |
| Cut surface | flat, slightly crumbly | slightly crumbly | fine, crumbly |

TABLE 16

| Antiperspirant stick, silicone-free | | | |
|---|---|---|---|
| Ingredients | 1 | 2 | 3 |
| Sebacic acid di-C16/18-ester | 14.70 |  | 14.70 |
| Lanette ® 18 |  | 14.70 |  |
| Cutina ® HR | 3.70 | 3.70 | 3.70 |
| Cetiol ® B | 29.35 | 29.35 | 17.50 |
| Synfluid ® 2 cSt | 29.35 | 29.35 |  |
| Rezal ® 36GP | 22.90 | 22.90 | 22.90 |
| Arlamol ® HD |  |  | 17.50 |
| Cetiol ® OE |  |  | 9.00 |
| Cetiol ® S |  |  | 14.70 |

APPENDIX

1) Arlamol® HD—INCI: Heptamethylnonane
   Manufacturer: Uniqema
2) Cetiol® B—INCI: Dibutyl Adipate
   Manufacturer: Cognis Deutschland GmbH & Co. KG
3) Cetiol® OE—INCI: Dicaprylyl Ether
   Manufacturer: Cognis Deutschland GmbH & Co. KG
4) Cetiol® S—INCI: Diethylhexylcyclohexane
   Manufacturer: Cognis Deutschland GmbH & Co. KG
5) Cutina® HR—INCI: Hydrogenated Castor Oil
   Manufacturer: Cognis Deutschland GmbH & Co. KG
6) Dow Corning® 245—INCI: Cyclomethicone
   Manufacturer: Dow Corning
7) Edenor® OSSG—INCI: 12-Hydroxystearic Acid
   Manufacturer: Cognis Deutschland GmbH & Co. KG
8) Lanette® 18—INCI: Stearyl Alcohol
   Manufacturer: Cognis Deutschland GmbH & Co. KG
9) Rezal® 36 GP—INCI: Aluminum Zirconium Tetrachlorohydrex GLY
   Manufacturer: Reheis
10) Synfluid® 2 cSt—INCI: Hydrogenated Didecene
    Manufacturer: Chevron

We claim:

1. A water-free cosmetic stick composition with a melting point of at least 30° C. containing:
   (a) at least one dicarboxylic acid diester of a C6-C18 dicarboxylic acid with C12-C22 fatty alcohols,
   (b) at least one oil component, (c) at least one member selected from the group consisting of inorganic astringent salts, deodorant components and a pigment;

wherein the dicarboxylic acid diester has a melting point of at least 30° C.

2. The composition as claimed in claim 1, wherein, at least one compound containing iron oxide is present as the pigment.

3. The composition as claimed in claim 1, containing:
(a) 5 to 40% by weight of at least one diester of a C6-C18 dicarboxylic acid with C12-C22 fatty alcohols,
(b) 30 to 80% by weight of at least one oil component,
(c) 10 to 40% by weight of at least one inorganic astringent salt.

4. The composition as claimed in claim 1, wherein, the dicarboxylic acid diester has a melting point of at least 50° C.

5. The composition as claimed in claim 1, wherein, the dicarboxylic acid component is an unbranched, saturated C6-C18 dicarboxylic acid.

6. The composition as claimed in claim 1, wherein the alcohol component is selected from unbranched, saturated C16-C22 fatty alcohols.

7. The composition as claimed in claim 1, wherein the inorganic perspiration-inhibiting salt is at least one member selected from the group consisting of astringent aluminum compounds, aluminum-zirconium compounds or zinc salts.

8. The composition as claimed in claim 1, wherein, the at least one oil component comprises a member selected from the group consisting of dialkyl ethers, dialkyl carbonates, hydrocarbons and mixtures thereof.

9. An antiperspirant stick composition comprising an inorganic astringent salt and a dicarboxylic acid diester of a C6-C18 dicarboxylic acid with a C12-C22 fatty alcohol, wherein the dicarboxylic acid diester has a melting point of at least 30° C.

10. The composition of claim 9 which is water-free.

11. Make-up sticks and/or lipstick compositions comprising a pigment and a dicarboxylic acid diester of a C6-C18 dicarboxylic acid with a C12-C22 fatty alcohol, wherein the dicarboxylic acid diester has a melting point of at least 30° C.

12. The composition of claim 5, wherein the dicarboxylic acid component is a C9-C18 dicarboxylic acid.

13. The composition of claim 5 wherein the dicarboxylic acid is a C12-C18 dicarboxylic acid.

14. The composition of claim 1, wherein the dicarboxylic acid diester has a melting point in a range of 50° C. to 55° C.

15. The composition of claim 11 which is water-free.

* * * * *

UNITED STATES PATENT AND TRADEMARK OFFICE
CERTIFICATE OF CORRECTION

| | | |
|---|---|---|
| PATENT NO. | : 8,518,385 B2 | Page 1 of 1 |
| APPLICATION NO. | : 11/886621 | |
| DATED | : August 27, 2013 | |
| INVENTOR(S) | : Dierker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1777 days.

Signed and Sealed this
Fourteenth Day of April, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,518,385 B2 | Page 1 of 1 |
| APPLICATION NO. | : 11/886621 | |
| DATED | : August 27, 2013 | |
| INVENTOR(S) | : Dierker et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1532 days.

Signed and Sealed this
Eighth Day of September, 2015

Michelle K. Lee
*Director of the United States Patent and Trademark Office*